(12) United States Patent
Teske

(10) Patent No.: US 8,675,338 B2
(45) Date of Patent: *Mar. 18, 2014

(54) ELECTRICAL FEEDTHROUGH OF A CAPACITOR FOR MEDICAL IMPLANTS AND METHOD FOR THE PRODUCTION AND USE THEREOF

(75) Inventor: Josef Teske, Hallstadt (DE)

(73) Assignee: Biotronik SE & Co. KG, Berlin (DE)

( * ) Notice: Subject to any disclaimer, the term of this patent is extended or adjusted under 35 U.S.C. 154(b) by 284 days.

This patent is subject to a terminal disclaimer.

(21) Appl. No.: 13/071,974

(22) Filed: Mar. 25, 2011

(65) Prior Publication Data

US 2011/0235239 A1 Sep. 29, 2011

Related U.S. Application Data

(60) Provisional application No. 61/318,403, filed on Mar. 29, 2010.

(51) Int. Cl.
*H01G 4/35* (2006.01)
*H01G 4/236* (2006.01)

(52) U.S. Cl.
USPC .......................................... 361/302; 361/307

(58) Field of Classification Search
USPC .................................................. 361/302, 307
See application file for complete search history.

(56) References Cited

U.S. PATENT DOCUMENTS

| | | | | |
|---|---|---|---|---|
| 5,333,095 | A | * | 7/1994 | Stevenson et al. ............ 361/302 |
| 5,734,546 | A | * | 3/1998 | Kuriyama et al. ............ 361/523 |
| 6,031,710 | A | * | 2/2000 | Wolf et al. .................... 361/302 |
| 6,801,424 | B1 | * | 10/2004 | Nielsen et al. ................ 361/517 |
| 6,899,976 | B2 | * | 5/2005 | Larson et al. ................. 429/180 |
| 8,131,369 | B2 | * | 3/2012 | Taylor et al. .................... 607/36 |
| 8,326,425 | B2 | * | 12/2012 | Sprain et al. .................... 607/36 |
| 2005/0060003 | A1 | * | 3/2005 | Taylor et al. .................... 607/36 |
| 2008/0060844 | A1 | * | 3/2008 | Teske et al. .................. 174/667 |
| 2011/0004283 | A1 | * | 1/2011 | Stevenson et al. ............ 607/116 |

* cited by examiner

*Primary Examiner* — David M Sinclair
(74) *Attorney, Agent, or Firm* — Buchanan Ingersoll & Rooney PC

(57) ABSTRACT

A feedthrough of an electrolyte or other capacitor, in particular for use in a medical-electronic implant, is provided having a terminal pin which has a section which can be soft soldered at least in the interior of the electrolyte capacitor, an aluminum flange enclosing the terminal pin, and a glass solder plug which hermetically seals the terminal pin in relation to the aluminum flange.

20 Claims, 11 Drawing Sheets

ELECTRICAL FEEDTHROUGH OF A CAPACITOR FOR MEDICAL IMPLANTS AND METHOD FOR THE PRODUCTION AND USE THEREOF

RELATED APPLICATION

This patent application claims the benefit of co-pending U.S. Provisional Patent Application No. 61/318,403, filed on Mar. 29, 2010, which is hereby incorporated by reference in its entirety.

TECHNICAL FIELD

The present invention relates to a so-called feedthrough (the terminal pin area) of an electrolyte, tantalum, niobium, or other capacitor and, additionally, to a method for the production and use of such a feedthrough and a capacitor having such a feedthrough.

BACKGROUND OF THE INVENTION

Capacitors, such as electrolyte, tantalum, or niobium capacitors for use in medical-electronic implants, such as, for example, defibrillators, are known in various embodiments and in practical use. Constructions based on the aluminum foils for high-voltage applications, so-called A1-HV capacitors, are customary in entertainment electronics. Such constructions have a seal made of rubber-like materials or plastics which, however, does not prevent an escape (very slow) of electrolyte components from the capacitor interior to the outside. A restricted lifetime and reliability and the danger of contamination of the interior of the devices in which they are installed, i.e., especially the noted implants, are thus caused. Constructions based on tantalum or niobium, so-called Ta—HV or Nb—HV capacitors, are also known, which are significantly more heavy than A1-HV capacitors, however, and whose production technology is difficult to control.

The present invention is based on the object of disclosing an improved construction for electrolyte capacitors of the A1-HV type, and also for the other cited tantalum, niobium, or other capacitor types, which provides them in particular with improved reliability, longer lifetime, and improved usability in medical-electronic implants.

SUMMARY

This object is achieved according to its device aspect by a feedthrough having the features of the apparatus claims and, according to relatively independent method aspects, by a method having the features of the method claims. Expedient refinements of the idea of the present invention are the subject matter of the dependent claims.

The present invention includes the essential aspect of implementing the feedthrough according to the species as hermetically sealed, the feedthrough separating the capacitor interior from the capacitor exterior hermetically sealed from one another. Furthermore, it includes the aspect of providing a glass solder plug which electrically insulates the terminal pin in relation to the aluminum flange. The terminal pin is implemented as compatible for this purpose with the capacitor interior at least on a section lying in the interior of the capacitor. In connection with the present invention, it is significant that exclusively aluminum surfaces and insulator surfaces are provided in the interior of the capacitor, from which no foreign ions are discharged into the electrolytes, which impermissibly increase its self-discharge and/or could impair its high-voltage stability. The same measures apply accordingly for tantalum, niobium, or other capacitor types.

An expedient embodiment of the present invention provides that the terminal pin, in the area of its length in which it is in contact with the glass solder plug, has at least one core made of a material which has approximately the same or a lesser coefficient of thermal expansion as the glass solder. In this way, impermissibly high mechanical tension strains in the glass solder may be fundamentally avoided during the production and the use of the finished feedthrough. The terminal pin or its core, in the area of its length in which it is in contact with the glass solder plug, can especially include Pt, Pt/Ir, FeNi, FeNiCo, FeCr, Nb, Ta, Mo, W, Cr, FeCr, V, Ti, and further metals or their alloys.

In a further embodiment of the present invention, the section of the terminal pin in the interior of the electrolyte capacitor, which is more important for electrochemistry, is an aluminum pin, an aluminum plate, or an aluminum foil. For this purpose, the aluminum pin, the aluminum plate, or the aluminum foil is electrically conductively attached to a section of the terminal pin made of another material, in particular soldered, welded, plugged, crimped, or glued on in an electrically conductive manner. Aluminum as the interior material of the terminal pin is completely compatible with the remaining construction of an A1-HV capacitor especially and is free of interfering ion escape effects. These advantages may also be achieved in an alternative embodiment of the present invention in that the section of the terminal pin in the interior of the electrolyte capacitor, which is important for electrochemistry, has an aluminum coating of a section made of another material.

For expedient processing using the glass solder in the sealing section of the feedthrough, a design is advisable in which a pin made of Pt, Pt/Ir, FeNi, FeNiCo, FeCr, Nb, Ta, Mo, W, Cr, FeCr, V, Ti, and further metals or their alloys is attached, in particular soldered, welded, plugged, crimped, or glued onto the aluminum pin or the aluminum plate. To make the further process control easier, in particular the exterior terminal pin can have a so-called nailhead, be flattened, curved, be provided with an attached bushing or disk, or otherwise be suitably formed. The nailhead makes subsequent soft soldering of the external terminal easier, especially also using a reflow method.

A further preferred construction of the proposed feedthrough is distinguished in that the terminal pin in the aluminum flange is enclosed by a ceramic ring, in particular made of Al2O3 ceramic, so that the ceramic ring forms a terminus for the glass solder plug during the soldering process and thus positively influences the glass shape, so that the glass solder plug can achieve a hermetic seal during the production of the feedthrough at a higher yield. Such a combined glass-ceramic feedthrough additionally obtains high mechanical stability through the high-quality rigid ceramic components and a high-quality and reliable electrical insulation section is also achieved by the ceramic components on the adjacent surfaces of (aluminum) flange and terminal pin. In particular, it offers the glass solder plug mechanical protection in relation to lateral force actions (bending forces), which may engage on the terminal pin.

In a further embodiment of the present invention, a filler which encloses the terminal pin, or a coating, is provided on the interior of the glass solder plug. The filler or the coating is especially dimensioned and situated so that it masks a joint in the terminal pin if the joint is incompatible in relation to the capacitor interior and cannot be kept sufficiently separate from the capacitor interior by the glass solder plug. If the glass solder plug itself is incompatible with the capacitor interior, the filler or the coating covers the surface of the glass solder plug accessible to the capacitor interior. This filler or this coating ensures the compatibility, which is important for the function of the capacitor, between the materials provided in its interior, which could not be ensured by the materials to be used on the exterior to achieve hermetic tightness. The filler can also be provided as a plug, or also as a covering, coating, vapor-deposited coating, inter alia, and is to cover all surfaces which are incompatible with the internal materials.

An expedient method control for producing the feedthrough, which especially allows the use of terminal pin materials having a coefficient of thermal expansion significantly different from the glass solder, is distinguished in that the terminal pin is cooled using a heat sink during the production of the glass solder plug. Because the terminal pin remains cooler than the glass in this case, the thermal tensions which occur otherwise may be controlled enough that hermetically sealed soldering is achieved. The heat introduction into the glass solder can be performed, for example, by IR radiation (for example, of a CO2 laser) or inductive heat coupling via the surrounding flange, inter alia.

Moreover, it is advantageous under this aspect to keep the amount of glass solder low and to keep the effective sealing interface between the glass solder and the terminal pin small, in order to keep the absolute values of the mechanical tensions low between the glass solder plug and pin, as a result of mutual large differences in the coefficients of thermal expansion.

DESCRIPTION OF THE DRAWINGS

Moreover, advantages and expedient features of the present invention result from the following description of exemplary embodiments and aspects of the embodiments on the basis of the figures. In the figures.

DETAILED DESCRIPTION

Figure 1:
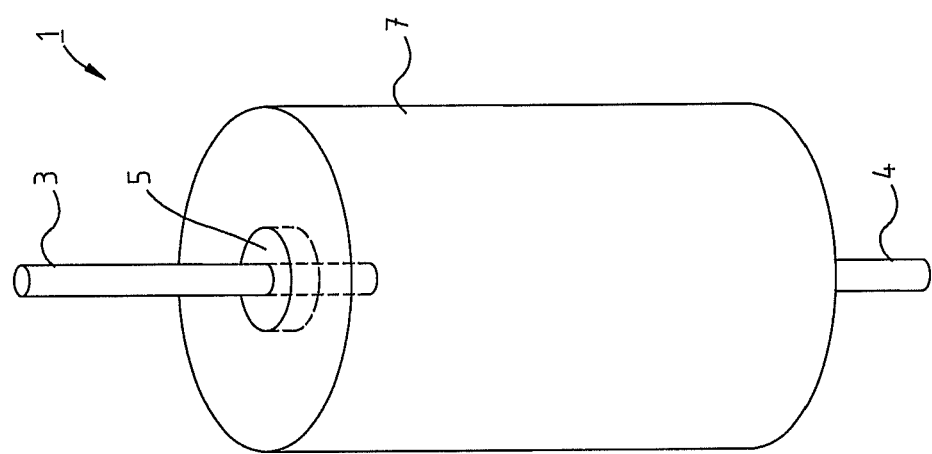
FIG. 1 shows an overall view of an (electrolyte) capacitor.

FIG. 1 shows a perspective illustration of a known construction of an electrolyte capacitor 1 having two terminal pins 3 and 4, and a feedthrough 5 being shown schematically outlined on a front side of a housing 7.

Figure 2:
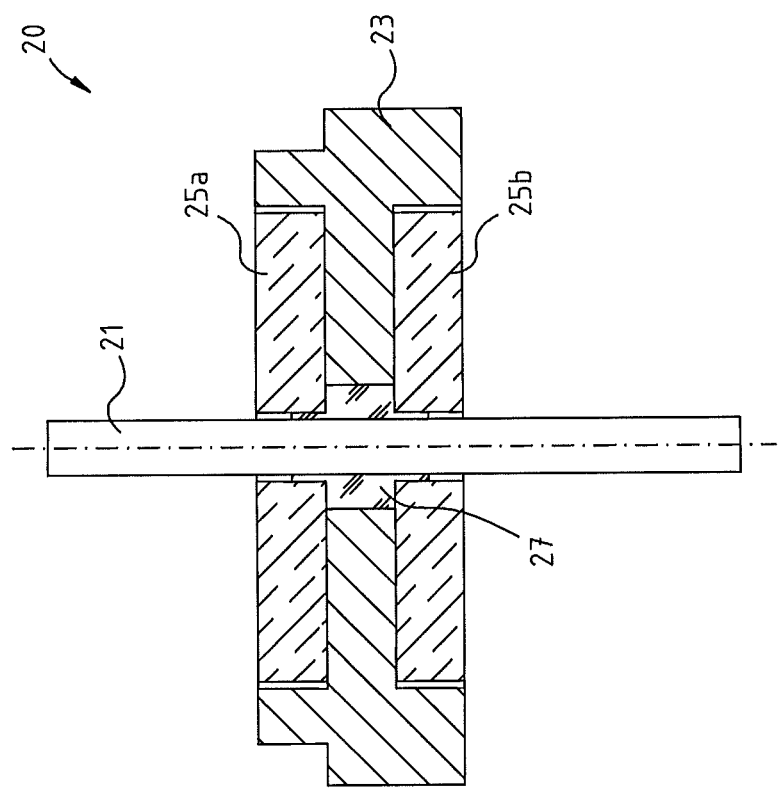
FIGS. 2-4 show longitudinal sectional illustrations of feedthroughs according to embodiments of the present invention.

FIG. 2 shows, as an embodiment of the present invention, a feedthrough 20 having an aluminum terminal pin 21, an aluminum flange 23 provided on the top and bottom with flat cylindrical recesses, and ceramic discs 25a, 25b, each lying in the aluminum flange 23, and having a central opening for the passage of the aluminum pin 21. A housing wall (not shown here) adjoins the construction on the exterior of the aluminum flange 23, and a glass solder plug 27 is located between the central part of the aluminum flange 23 and the inner walls of the central openings of the ceramic discs 25a, 25b and the external surface of the pin 21, which hermetically seals both the pin 21 and also the aluminum flange 23 in relation to the surrounding surfaces, so that overall a hermetic seal results between the capacitor interior and exterior, which is also mechanically stable, electrically insulating, dimensionally accurate, has long-term stability, and is geometrically compact at a high yield.

A low-melting-point glass solder having a melting temperature significantly below that of the aluminum (660° C.) is to be used as the glass solder, for example, a lead-containing solder of the type G 017-052 from Schott having a soldering temperature of approximately 410° C. or a lead-free solder of the type G 018-249, also from Schott, having a soldering temperature of 500° C. Tensions because of the coefficients of thermal expansion, which deviate from one another, of the aluminum pin and aluminum flange, on the one hand, and the glass solder, on the other hand, may be extensively avoided by the special constructive design, which includes the use of a very small quantity of glass to generate the glass solder plug 27. Furthermore, cooling of the pin 21 via a heat sink is to be viewed as advisable in this meaning.

Figure 3:
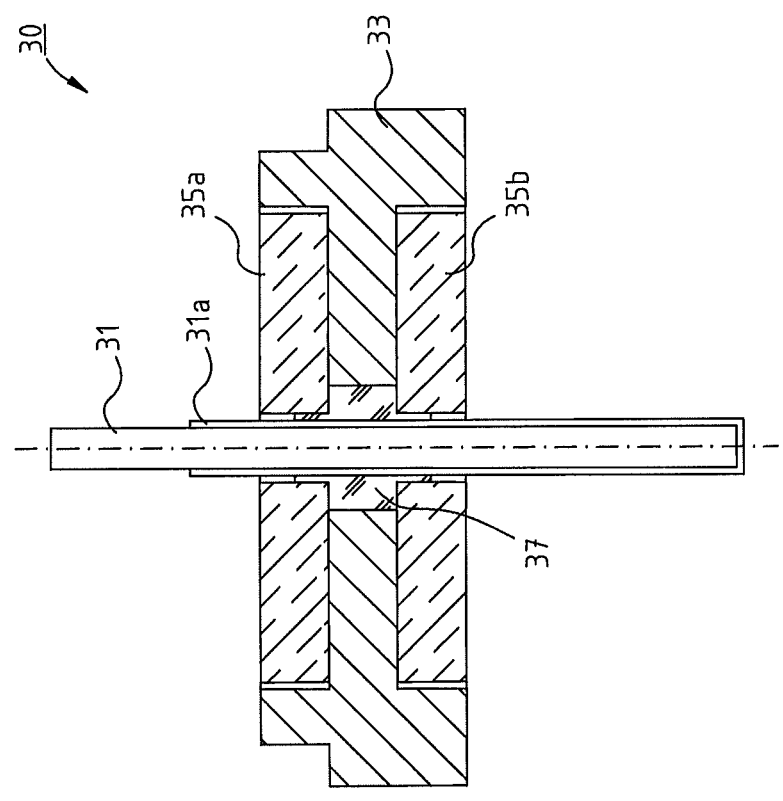

FIG. 3 shows a construction of a further feedthrough 30 which is fundamentally similar to the embodiment according to FIG. 2. Identical or similar parts are identified using reference numerals based on FIG. 2, but in the thirty series of numbers, and are not explained once again here. The essential difference from the embodiment according to FIG. 2 includes the use of a pin 31 made of platinum. This pin is provided with an aluminum coating 31a, which includes at least the capacitor-interior part of the pin located inside the flange 33 and the ceramic discs 35a and 35b and the interior section on the glass plug 37. The coating can also, as indicated in FIG. 3, extend up into the capacitor-exterior part of the pin, so as not to impair the electrochemical processes in the glass solder, which play a role during the high-temperature soldering. Using this construction of the terminal pin 31, it is better adapted to the thermal coefficient of expansion of the glass, on the one hand, and the exposure of surfaces which are incompatible with the remaining materials in the interior of the capacitor is avoided by the aluminum coating, on the other hand. The aluminum coating can be provided with an adequate oxide layer in the capacitor, and the pin can be soldered, welded, plugged, crimped, or glued on in an electrically conductive manner from the outside.

Figure 4:
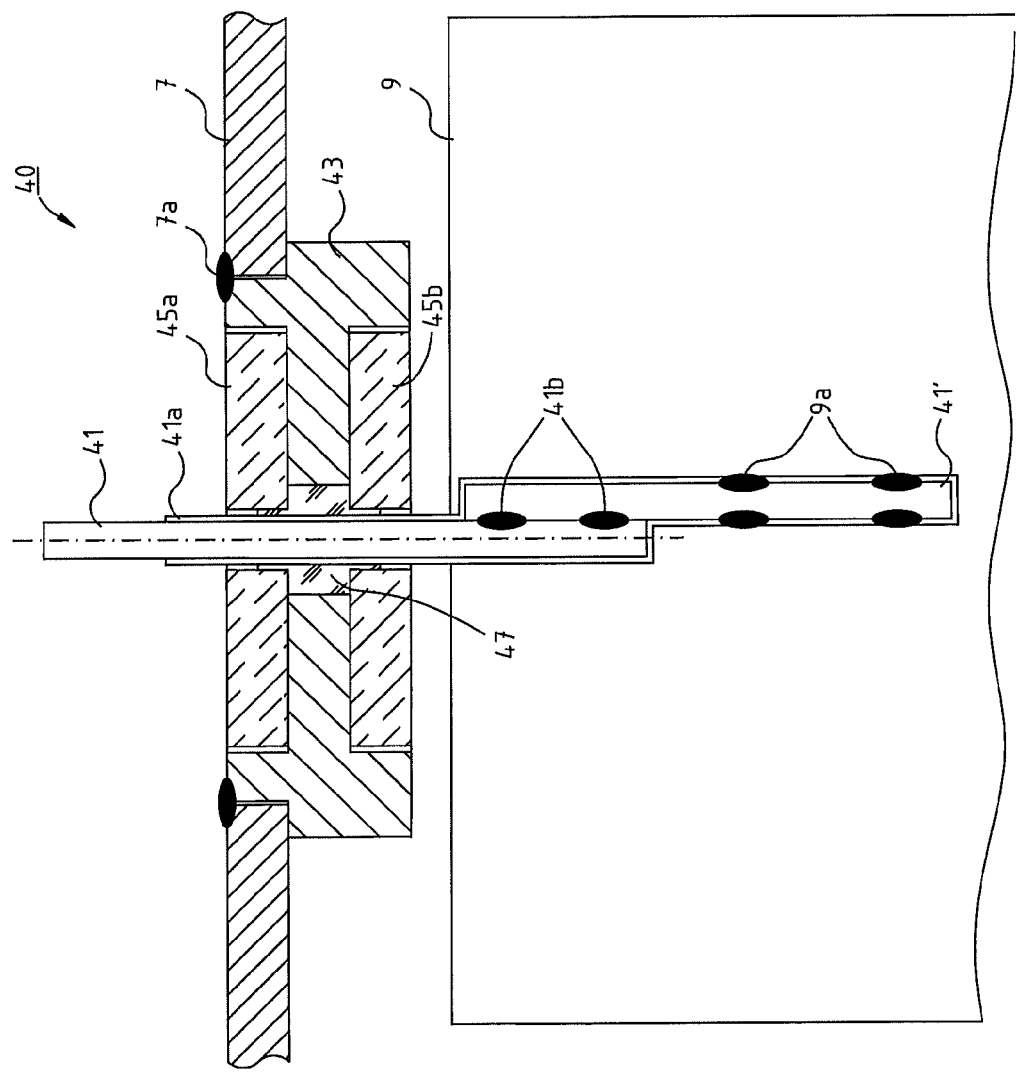

FIG. 4 shows, as a refinement of the embodiment shown in FIG. 3, a further feedthrough 40, where reference numerals based on FIGS. 2 and 3 are again used, but in the forty series of numbers. In addition to the actual feedthrough, in this illustration the adjoining sections of the housing 7 are also shown, which are connected gas-tight via a weld seam 7a to the aluminum flange 43. Furthermore, the figure shows an aluminum capacitor plate 9, which forms an essential functional component of the capacitor construction, and joints and spot welds 9a for its connection to the terminal pin.

A further special feature of the construction according to FIG. 4 is that the terminal pin is constructed here from an external pin 41 made of a material other than Al, such as, but not limited to, Pt, Pt/Ir, FeNi, FeNiCo, FeCr, Nb, Ta, Mo, W, Cr, FeCr, V, or Ti, and an interior pin 41' made of Al, which are connected to one another via spot welds 41b. The entire capacitor-interior surface of both partial terminal pins 41, 41', including the section located inside the flange 43 and the ceramic discs 45a and 45b, and the surface of the spot welds 41b are covered with an aluminum coating 41a, which is compatible with the capacitor interior. It may be seen well in this figure that all surfaces facing toward the interior of the capacitor, namely those of the housing 7, the flange 43, the ceramic disc 45b, and the interior section of the terminal pin 41/41' include aluminum or a metal compatible therewith or a compatible ceramic. The aluminum coating 41a, which is located over the external pin 41, the internal pin 41', the joints 41b and 9a, and optionally also over the aluminum capacitor plate 9, can be provided in the capacitor with an adequate oxide layer (not shown), which then forms a functional dielectric material of the capacitor. A glass solder plug 47 is located between the central part of the aluminum flange 43 and the inner walls of the central openings of the ceramic discs 45a, 45b and the external surface of the pin 41, which hermetically seals both the pin 41 and also the aluminum flange 43 in relation to the surrounding surfaces.

Figure 5:
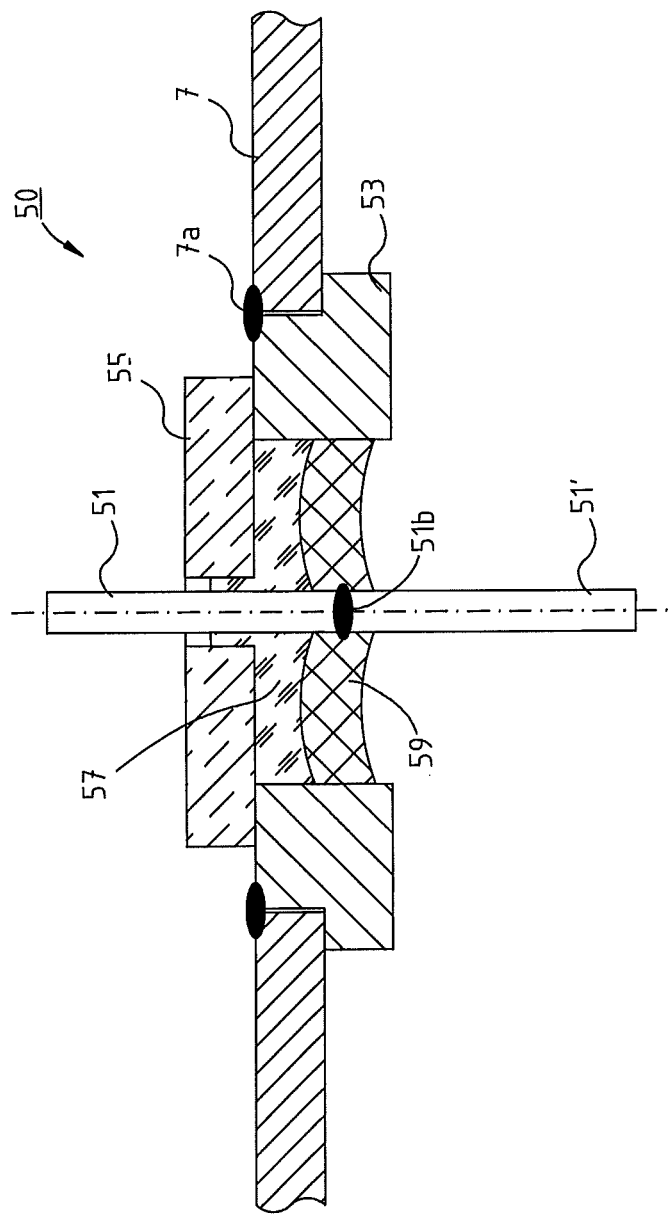
FIGS. 5-11 show longitudinal sectional illustrations of feedthroughs according to further embodiments of the present invention having additional filler.

FIG. 5 shows a further feedthrough 50 according to the present invention having an assembled terminal pin 51/51' made of a first pin section 51 made of, for example, Pt, Pt/Ir, FeNi, FeNiCo, FeCr, Nb, Ta, Mo, W, Cr, FeCr, V, or Ti, or an alloy made of these or similar materials, and a second pin section 51' made of aluminum. Both sections are connected to one another by a joint 51b, which is implemented by welding, soldering, crimping, electrically conductive gluing, or another suitable method.

Further differences from the preceding embodiments include the provision of an aluminum flange 53 having a constructively simpler design, and a single ceramic disc 55, which rests flatly on the top side of the flange 53 herein. The use of a pin section 51, whose coefficient of thermal expansion is adapted to or less than that of the glass plug 57, has the result that the common seal length may be greater than upon use of a pin made of aluminum than in the embodiments of FIGS. 2-4, so that the glass may be implemented having a greater volume, and a higher mechanical stability of the construction is thus achieved. Its surface facing toward the interior of the capacitor and the end of the external pin section 51 protruding slightly therefrom and the joint 51b are embedded in a filler plug 59. The filler can be rubber, a silicone compound, or a halogen-free or chlorine-free plastic, for example. The filler plug 59 ensures that no materials of the feedthrough construction which are incompatible with the materials typically used in the interior of the capacitor are exposed toward the capacitor interior.

In a design variant of FIG. 5, at least the joint and the part of the pin adjoining thereon and the transition to the exposed surface of the glass plug are covered by a filler plug and the capacitor interior is thus protected from incompatible components. The filler plug can also be implemented as a comparatively thin coating, which saves volume and which suppresses impermissible ion exchange of the incompatible components with the capacitor interior. If the glass plug is implemented from a compatible material in relation to the capacitor interior, it does not have to be completely covered by the filler plug or the coating.

In a further design variant of FIG. 5, the joint and additionally a part of the aluminum pin section can be partially or entirely enclosed by the glass plug. Even in the case of simultaneous enclosure of the joint and the part of the aluminum pin section adjoining thereon by the glass plug, the glass plug generally cannot ensure a hermetically sealed closure of these parts in relation to the capacitor interior because of the comparatively large coefficients of thermal expansion of the joint and the pin. This task is to be taken over in a preferred design variant by a filler plug or by a corresponding coating, which at least completely covers the transition from the glass plug to the pin or to the joint, and thus masks it in relation to the capacitor interior.

In a further design variant of FIG. 5, two ceramic rings enclose the glass plug on the exterior and interior, the two-part pin being guided through an opening of the ceramic rings and being enclosed hermetically sealed by the glass plug. The joint can be located entirely or partially inside the glass plug and entirely or partially inside the ceramic ring located in the capacitor interior. In a preferred design variant, at least the components incompatible in relation to the capacitor interior, i.e., the joint of the pin section and, if an incompatible glass plug material is selected, also the glass plug, are covered by a filler plug or a coating. The inner ceramic ring and the flange, as well as the housing, can be entirely or partially covered or wetted by the filler plug or the coating.

Figure 6:
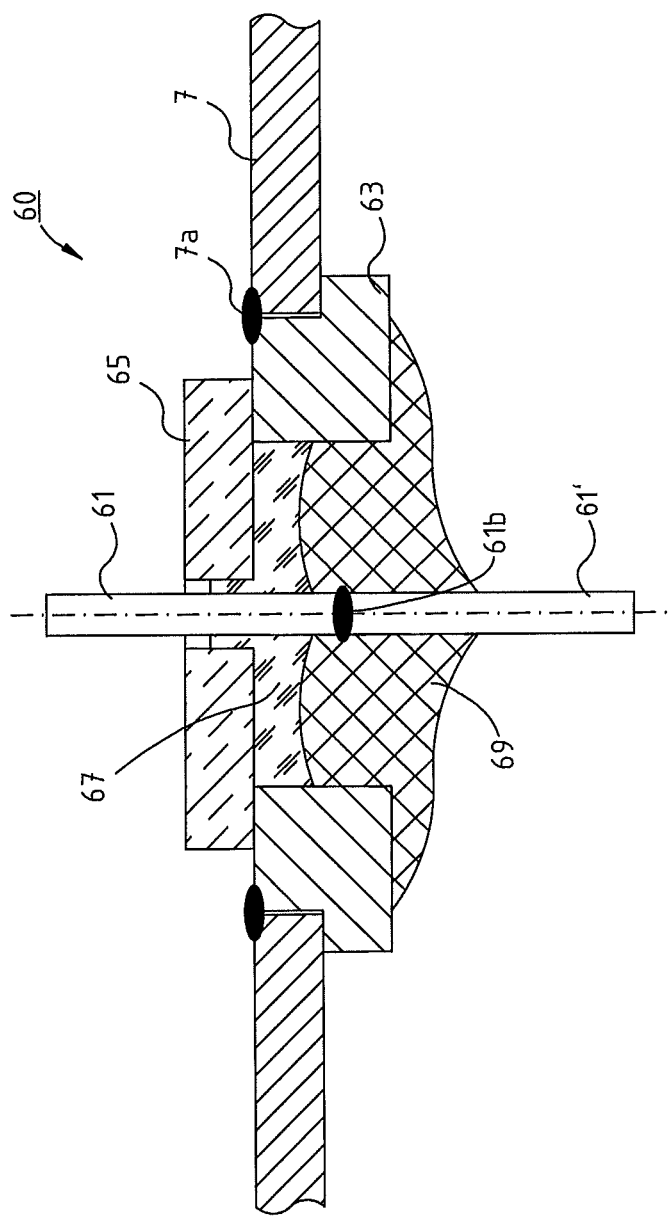

FIG. 6 shows a slight alteration of the design 60 shown in FIG. 5, in which the filler plug 69 completely fills up the hole of the flange 63 and wets a larger area of the inner terminal pin section 61'. This has the advantage that the joint 61b between the pin sections 61 and 61' no longer has to be located inside the hole of the flange 63 and can therefore be formed more easily. The design 60 includes a ceramic disc 65 and glass solder 67 surrounding the pin 61 in the area between the ceramic disc 65 and filler plug 69.

Moreover, the joint can also be a welded or soldered or electrically conductive glued joint, or the pin sections may be clamped to one another (via an additional element or via an opening (hole) or a gap of the two pins).

Figure 7:
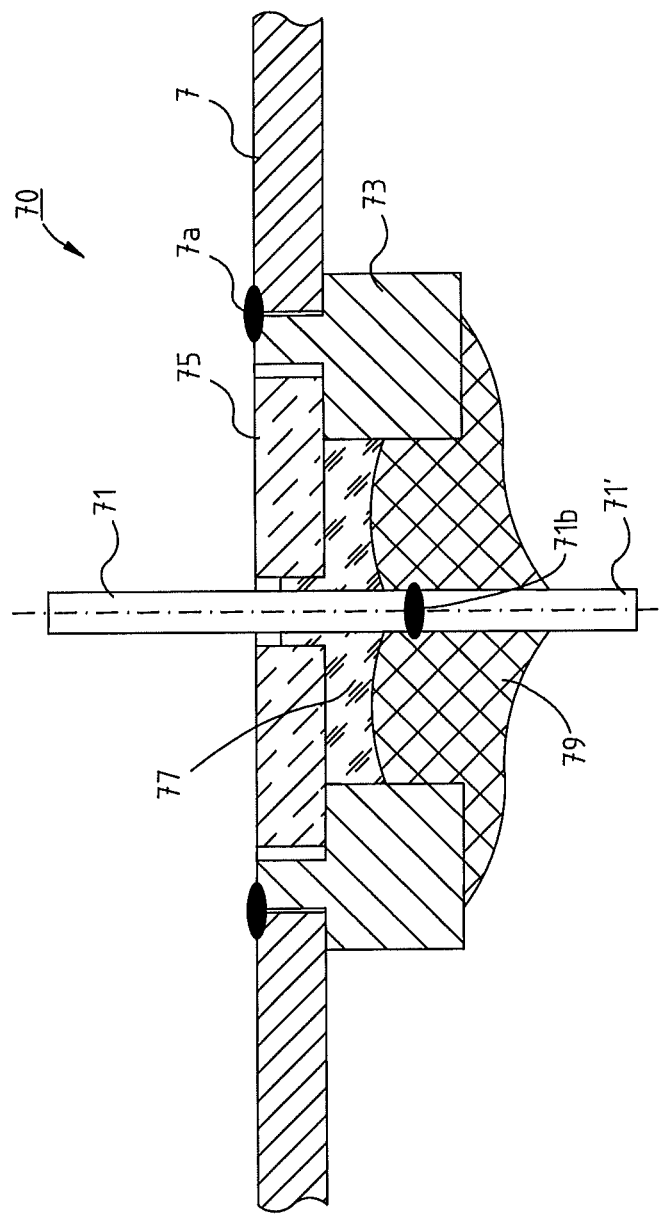

A further feedthrough 70 shown in FIG. 7 represents a slight alteration of the embodiment shown in FIG. 6, in which a widened recess is provided in the top side of the flange 73 and the ceramic disc 75 is inserted therein in such a way that its upper front face terminates approximately flush with the upper front face of the flange 73, and an essentially flat surface of the feedthrough and the associated capacitor front face is thus provided overall (with incorporation of the upper housing section 7). The design 70 includes a filler plug 79 which completely fills up the hole of the flange 73 and wets a larger area of the inner terminal pin section 71'. This has the advantage that the joint 71b between the pin sections 71 and 71' no longer has to be located inside the hole of the flange 73 and can therefore be formed more easily. The glass solder 77 surrounds the pin 71 in the area between the ceramic disc 75 and the filler plug 79. In a design variant which is not shown herein, this principle of having the embedded ceramic disc can also be transferred to a ceramic disc located on the interior of the capacitor. The ceramic disc(s) provided with a central opening take or takes over the task of centering the pin in relation to the central flange opening during the soldering of the glass/ceramic feedthrough in the production process.

Figure 8:
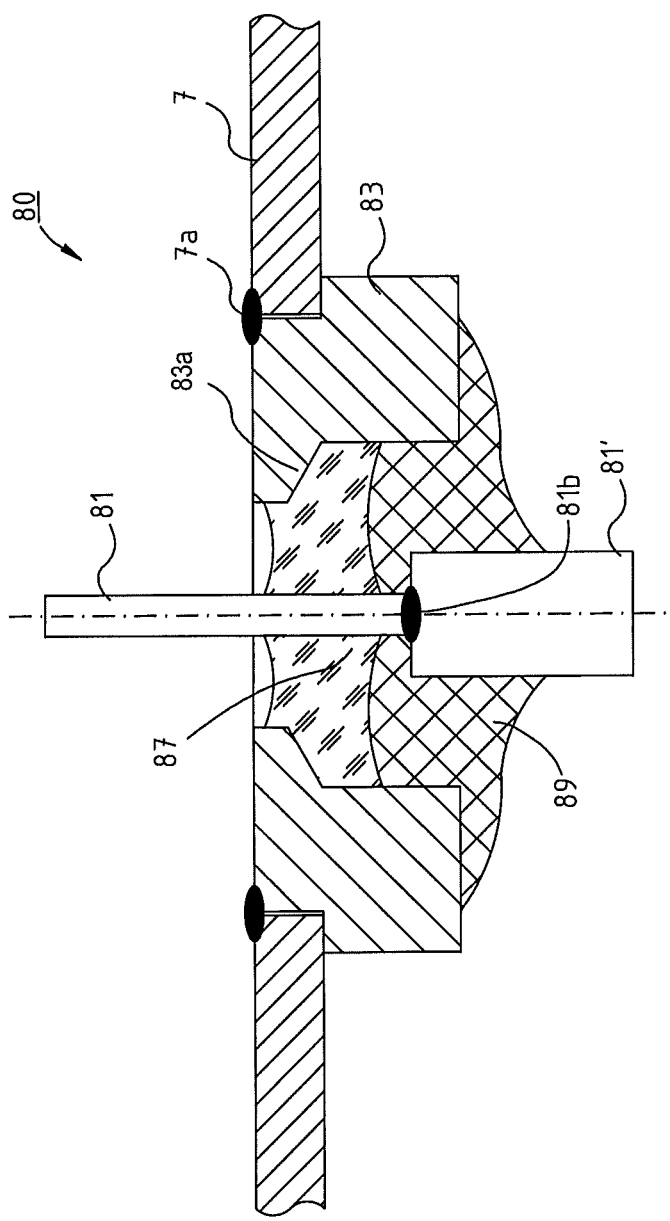

In the further feedthrough 80 shown in FIG. 8, the flange 83 has a further modified form, which allows the ceramic disc(s) provided in the other embodiments to be dispensed with. The filler plug 89 completely fills up the hole of the flange 83 and wets a larger area of the inner terminal pin section 81'. In order to ensure a favorable glass solder shape and a favorable position of the glass solder plug 87 in the flange 83, the flange 83 has a beveled section 83a pointing inward here, which positions the glass solder plug during the production process and takes over the mechanical function of the ceramic disc to a certain degree in application. The inner section 81' of the terminal pin is wider (and/or thicker) than the exterior pin section 81, in whose area the hermetically tight seal is produced via the glass solder, here as a design variant. The inner 81' and exterior 81 pins sections are connected at a joint 81b, which is surrounded by the filler plug 89. The inner section may further also be a plate of various forms, inter alia.

In a further design variant, the beveled section 83a can be dispensed with and the flange can thus have a continuous, cylindrical opening, the position of the glass solder plug in the opening of the flange then being established by corresponding measures during the production process, such as, for example, the use of centering units which cannot be wetted by the glass solder, such as, for example, graphite.

Figure 9:
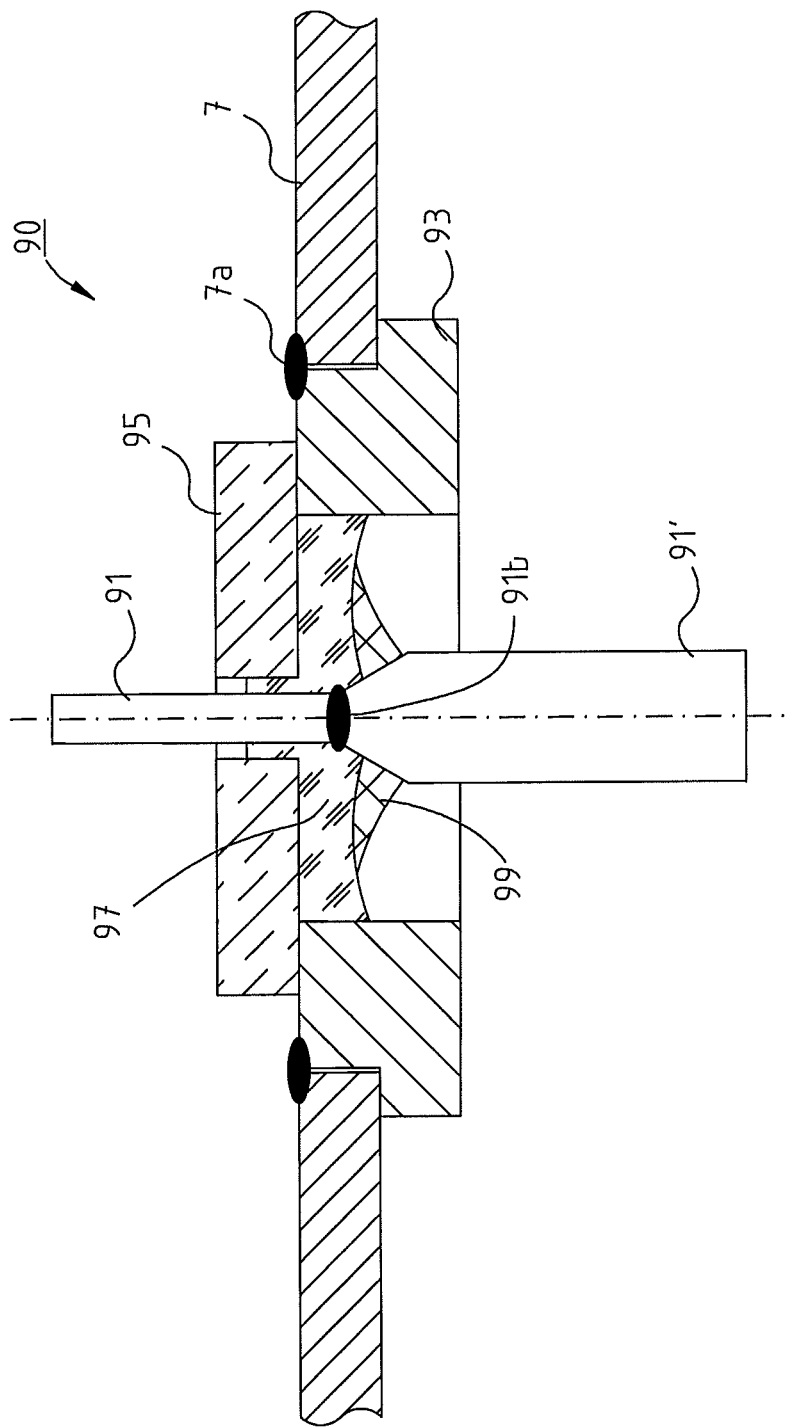

In the further feedthrough 90 shown in FIG. 9, the ceramic disc 95 is positioned on top of the flange 93 and rests flatly on the top side thereof. The inner section 91' of the terminal pin is wider (and/or thicker) than the exterior pin section 91. The inner section 91' has a beveled section pointing inward at the joint 91b. The joint 91b is positioned in and completely covered by the glass plug 97. The filler plug 99 covers the area near and/or around the joint 91b, but does not completely fill up the hole of the flange 93. In this embodiment, the glass plug 97 should be implemented from a compatible material in relation to the capacitor interior (such as the electrolyte) to protect the capacitor interior from incompatible components outside the capacitor.

Figure 10:
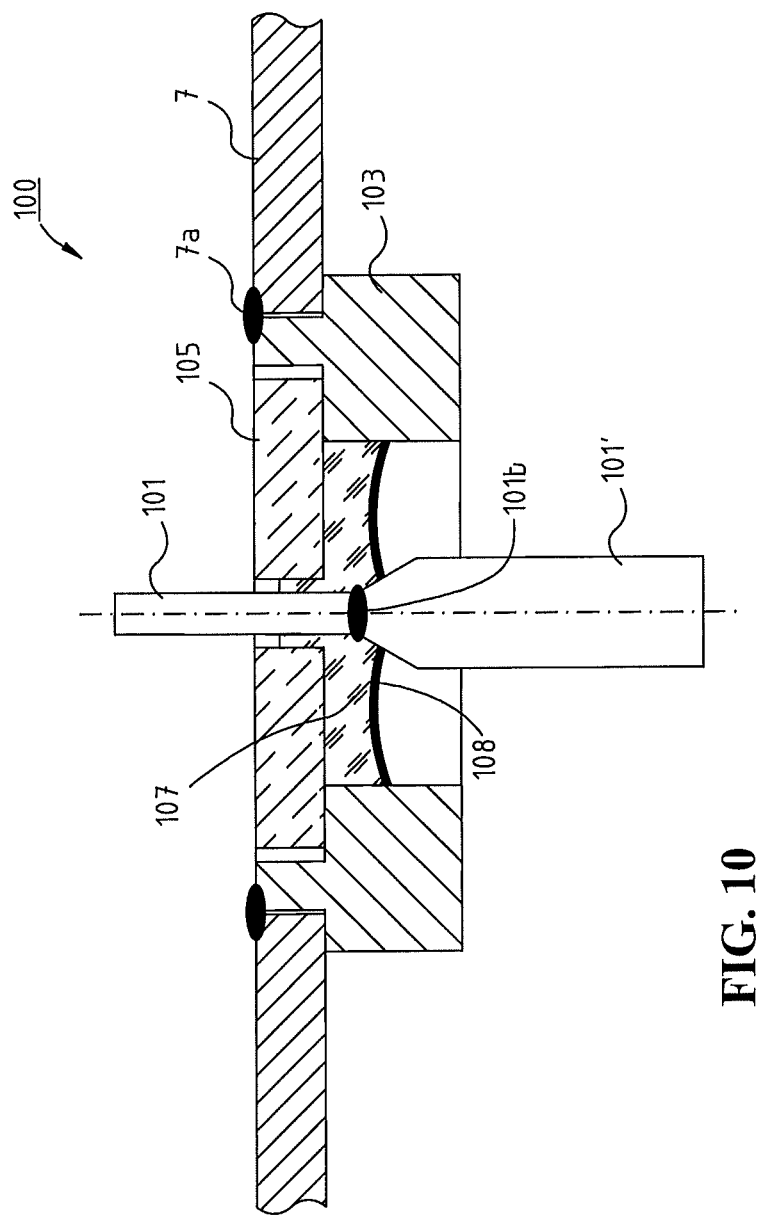

FIG. 10 shows a design alteration of the design 90 shown in FIG. 9. In FIG. 10, the feedthrough 100 includes a widened recess provided in the top side of the flange 103, and the ceramic disc 105 is inserted therein in such a way that its upper front face terminates approximately flush with the upper front face of the flange 103, and an essentially flat surface of the feedthrough and the associated capacitor front face is thus provided overall (with incorporation of the upper housing section 7). The inner section 101' of the terminal pin is wider (and/or thicker) than the exterior pin section 101, with the inner section 101' including a beveled section pointing inward at the joint 101b. The joint 101b is positioned in and completely covered by the glass plug 107. The filler plug is implemented as a comparatively thin coating 108, which completely covers the glass plug 107 and protects the capacitor interior from incompatible components. Implementing the filler plug as a coating 108 saves volume and which suppresses impermissible ion exchange of the incompatible components with the capacitor interior. The filler material can be rubber, a silicone compound, or a halogen-free or chlorine-free plastic, or polymers such as epoxy resin, Polyimide like Kapton® or Parylene®, for example.

Figure 11:
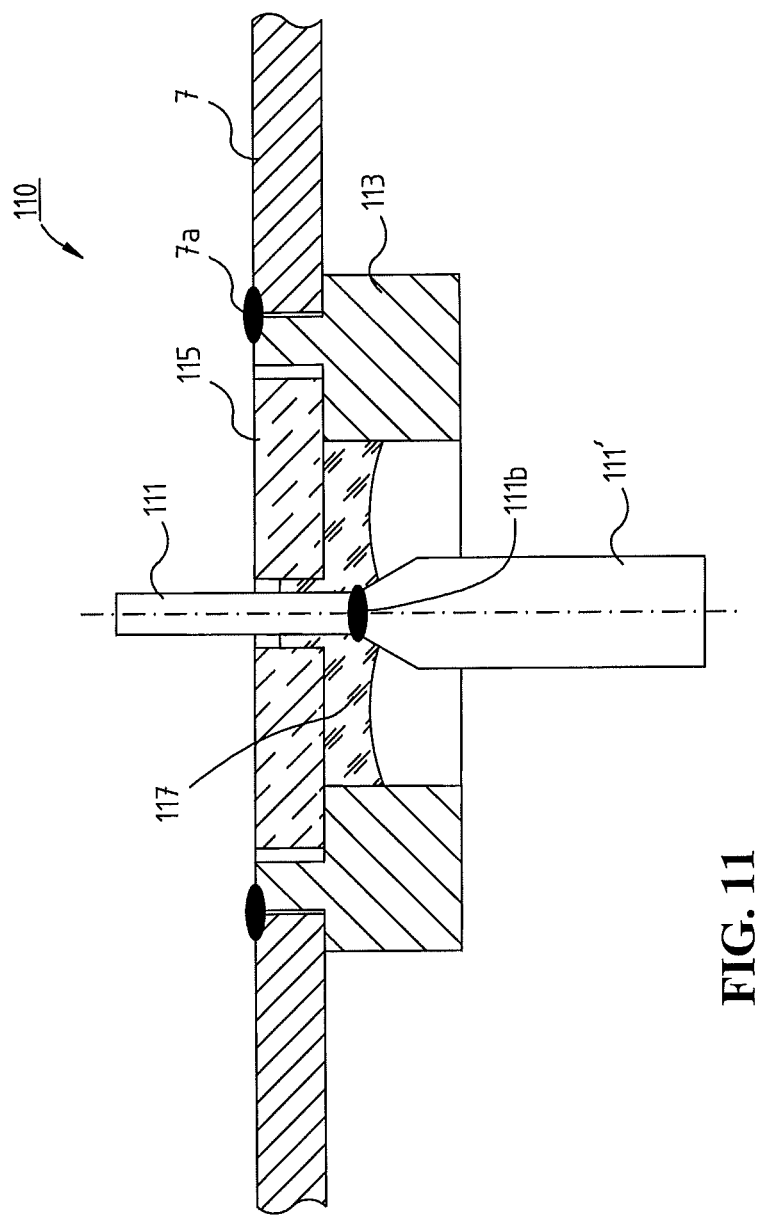

FIG. 11 shows a design alteration of the design 100 shown in FIG. 10, in which a widened recess provided in the top side of the flange 113, and the ceramic disc 115 is inserted therein in such a way that its upper front face terminates approximately flush with the upper front face of the flange 113, and an essentially flat surface of the feedthrough and the associated capacitor front face is thus provided overall (with incorporation of the upper housing section 7). In the feedthrough 110 shown in FIG. 11, the coating 108 (and filler plug) has been dispensed with. In this embodiment, the glass plug 117 is implemented from a compatible material in relation to the capacitor interior, thus allowing the coating and filler plug to be removed while still protecting the capacitor interior from incompatible components. The glass plug 117 at least completely covers the joint 111b of the exterior 111 and interior 111' pin sections, and this masks it in relation to the capacitor interior.

The embodiments of the present invention are not restricted to the above-described examples and emphasized aspects, but rather are also possible for various further capacitor types and the numerous alterations, which are within the scope of normal measures of one skilled in the art.

It will be apparent to those skilled in the art that numerous modifications and variations of the described examples and embodiments are possible in light of the above teachings of the disclosure. The disclosed examples and embodiments are presented for purposes of illustration only. Therefore, it is the intent to cover all such modifications and alternate embodiments as may come within the true scope of this invention, which is to be given the full breadth thereof. Additionally, the disclosure of a range of values is a disclosure of every numerical value within that range.

I claim:

1. A feedthrough of a capacitor for use in a medical-electronic implant comprising:

a terminal pin, which has a first section made of a first material compatible with the capacitor interior in the interior of the capacitor, and a second section made of a second material in the exterior of the capacitor, wherein the first and second sections are physically connected together at a joint;

an aluminum, titanium, tantalum, or niobium flange which encloses the terminal pin;

a glass solder plug which hermetically seals the terminal pin in relation to the flange; and a polymer filler enclosing the terminal pin and situated so that it covers the joint between the first and second sections.

2. The feedthrough according to claim 1, wherein the capacitor comprises an electrolyte, tantalum, or niobium capacitor.

3. The feedthrough according to claim 1, wherein the terminal pin has at least one core made of the second material, which has approximately the same or a lesser coefficient of thermal expansion as the glass solder, in the second section of its length in which it is in contact with the glass solder plug.

4. The feedthrough according to claim 3, wherein the second material of the terminal pin or its core, in the second section of its length in which it is in direct contact or in contact via a coating with the glass solder plug, is made of Pt, Pt/Ir, FeNi, FeNiCo, FeCr, Nb, Ta, Mo, W, Cr, FeCr, V, Ti, or an alloy with metals of this group.

5. The feedthrough according to claim 1, wherein the first section of the terminal pin, which is compatible with the capacitor interior, in the interior of the capacitor, is an aluminum pin, an aluminum plate, or an aluminum foil.

6. The feedthrough according to claim 5, wherein the aluminum pin, the aluminum plate, or the aluminum foil of the terminal pin first section is joined to the second section of the terminal pin made of the second material via soldering, welding, crimping, or gluing in an electrically conductive manner via the joint.

7. The feedthrough according to claim 1, wherein the first section of the terminal pin, which is compatible with the capacitor interior, in the interior of the capacitor, has an aluminum coating on a section made of another material.

8. The feedthrough according to claim 1, wherein the second section of the terminal pin in the exterior area of the capacitor is a pin or a plate made of the second material which can be soft soldered, the second material including nickel, iron, copper, palladium, gold, or silver, or an alloy with one of these metals.

9. The feedthrough according to claim 8, wherein an aluminum, tantalum, niobium, or titanium pin is joined on the pin or the plate made of the second material which can be soft soldered via soldering, welding, crimping, or gluing in an electrically conductive manner, or connected thereto via the glass solder plug.

10. The feedthrough according to claim 9, wherein the exterior nickel, iron, copper, palladium, gold, silver, or alloy pin of the terminal pin second section has a nailhead, a bushing, a flattened area, or a functional curvature.

11. The feedthrough according to claim 8, wherein the exterior nickel, iron, copper, palladium, gold, silver, or alloy pin of the terminal pin second section has a nailhead, a bushing, a flattened area, or a functional curvature.

12. The feedthrough according to claim 8, wherein an exterior soft soldering is executed on the terminal pin using a reflow method.

13. The feedthrough according to claim 1, wherein the terminal pin in the aluminum, titanium, tantalum, or niobium flange is enclosed by at least one ceramic ring, wherein the glass solder plug is implemented so that it hermetically seals a ring gap between the terminal pin and the ceramic ring.

14. The feedthrough according to claim 13, wherein the ceramic ring is made of Al2O3 ceramic.

15. The feedthrough according to claim 1, wherein the polymer filler which encloses the terminal pin at the joint is provided on the interior of the glass solder plug.

16. An electrolyte capacitor having a feedthrough according to claim 1.

17. A method for the production of a feedthrough according to claim 1, comprising the step of cooling the terminal pin using a heat sink during the generation of the glass solder plug.

18. The feedthrough according to claim 1, wherein the first section of the terminal pin has a first width that is greater than a second width of the second section of the terminal pin.

19. The feedthrough according to claim 18, wherein the terminal pin includes a tapered section adjacent the joint, the tapered section tapering from the first width of the first section to the second width of the second section.

20. The feedthrough according to claim 1, wherein the flange, at an outer surface of the capacitor, has a beveled section pointing inward.

* * * * *